United States Patent
McGill et al.

(10) Patent No.: US 7,556,775 B2
(45) Date of Patent: Jul. 7, 2009

(54) MICROELECTRO-MECHANICAL CHEMICAL SENSOR

(75) Inventors: Robert Andrew McGill, Lorton, VA (US); Ioana Voiculescu, Washington, DC (US); Gary K. Fedder, Turtle Creek, PA (US)

(73) Assignee: The United States of America as represented by the Secretary of the Navy, Washington, DC (US)

( * ) Notice: Subject to any disclaimer, the term of this patent is extended or adjusted under 35 U.S.C. 154(b) by 804 days.

(21) Appl. No.: 11/136,763

(22) Filed: May 25, 2005

(65) Prior Publication Data

US 2005/0276726 A1    Dec. 15, 2005

Related U.S. Application Data

(60) Provisional application No. 60/574,388, filed on May 25, 2004.

(51) Int. Cl.
- *G01N 27/00* (2006.01)
- *G01N 27/04* (2006.01)
- *G01N 27/12* (2006.01)

(52) U.S. Cl. .......... 422/88; 73/1.02; 73/24.01; 73/335.02; 73/335.05; 422/82.01; 422/82.02; 422/83; 422/96; 422/97; 422/98

(58) Field of Classification Search .......... 422/50, 422/88; 435/6; 73/35
See application file for complete search history.

(56) References Cited

U.S. PATENT DOCUMENTS

| 3,768,300 A | 10/1973 | Nemeth |
| 5,083,466 A * | 1/1992 | Holm-Kennedy et al. ........ 73/862.041 |
| 5,756,631 A * | 5/1998 | Grate ........ 528/26 |
| 5,807,758 A | 9/1998 | Lee et al. |
| 5,970,803 A | 10/1999 | Staples et al. |
| 6,171,378 B1 | 1/2001 | Manginell et al. |
| 6,442,997 B1 | 9/2002 | Megerle et al. |
| 6,497,141 B1 | 12/2002 | Turner et al. |

(Continued)

FOREIGN PATENT DOCUMENTS

WO    WO-03/071258    8/2003

(Continued)

OTHER PUBLICATIONS

Thaysen et al., "SU-8 Based Piezoresistive Mechanical Sensor," Jan. 2002, IEEE, p. 320-323.*

(Continued)

*Primary Examiner*—Tony G Soohoo
*Assistant Examiner*—Robert Eom
(74) *Attorney, Agent, or Firm*—John J Karasek; Sally A Ferrett (57) ABSTRACT

A microelectro-mechanical chemical sensor includes an active cantilever beam having a chemically selective material layer disposed thereon and at least one, preferably two, resistors with the resistance corresponding to the cantilever beam deflection. The sensor also has at least two, and preferably four, auxiliary cantilever beams adjacent to the active cantilever and attached to the same substrate, each having a piezoresistor disposed thereon. The piezoresistors are elements of a Wheatstone bridge, and the Wheatstone bridge output indicates the amount of a predetermined target chemical sorbed by the chemically selective material layer. The sensor is electrostatically actuated in order to monitor the resonant frequency.

24 Claims, 7 Drawing Sheets

U.S. PATENT DOCUMENTS

| | | | |
|---|---|---|---|
| 6,527,835 | B1 | 3/2003 | Manginell et al. |
| 6,575,020 | B1 | 6/2003 | de Charmoy Grey et al. |
| 6,660,230 | B2 | 12/2003 | McGill et al. |
| 6,666,907 | B1 | 12/2003 | Manginell et al. |
| 6,668,627 | B2 | 12/2003 | Lange et al. |
| 6,866,819 | B1 * | 3/2005 | Chandra et al. ............... 422/50 |
| 2003/0062193 | A1 | 4/2003 | Thaysen et al. |
| 2004/0000705 | A1 | 1/2004 | Huppenthal et al. |
| 2005/0095722 | A1 | 5/2005 | McGill et al. |
| 2005/0226778 | A1 | 10/2005 | Houser et al. |

FOREIGN PATENT DOCUMENTS

| | | |
|---|---|---|
| WO | WO-03/104784 | 12/2003 |
| WO | WO-2004/083802 | 9/2004 |

OTHER PUBLICATIONS

Chen et al., "Adsorption-induced surface stress and its effects on resonance frequency of microcantilevers," Apr. 15, 1995, J. Appl. Phys, p. 3618-3622.*

H. Baltes, D. Lange, A. Koll, "The electronic nose in Lilliput," IEEE Spectrum, Sep. 1998, pp. 35-38.

H. P. Lang, R. Berger, F. Battiston, J. P. Ramseyer, E. Meyer, C. Andreoli, J. Brugger, P. Vettiger, M. Despont, T. Mezzacasa, L. Scandella, H. J. Guntherodt, C. Gerber, J. K. Gimzewski, "A chemical sensor based on micromechanical cantilever array for the identification of gases and vapors", *Apply. Phys. A 66*, pp. S61-S64, 1998.

R. A. McGill, M. H. Abraham, J. W. Grate, "Choosing polymer coatings for chemical sensors," *CHEMTECH 24*, pp. 27-37, 1994.

Voiculescu, I., Zaghloul, M., McGill, R.A., "Design, Fabrication, and Modeling of Microbeam Structures for Gas Sensors in CMOS Technology"; Circuits and Systems, 2003, ISCAS '03, Proceedings of the 2003 International Symposium vol. 3, May 25-28, 2003, pp. III-922-III-925.

Guillou, D.F., Santhanam, S., Carley, L.R., "Laminated, sacrificial-poly MEMS technology in standard CMOS", Sensors and Actuators, vol. 85 (2000), p. 346-355.

Houser, E.J., Simonson, D.L., Stepnowski, J.L., McGill, R.A. "Linear and Hyperbranched Hydrogen Bond Acidic Poly(silylene methylene)s for Chemical Sensor Applications", Polymeric Materials, Science & Engineering, 2003, vol. 88, p. 548.

Xie, H., Fedder, G.K., "Vertical comb-finger capacitive actuation and sensing for CMOS-MEMS", Sensors and Actuators A: Physical, vol. 95, Issue 2-3, pp. 212-221, 2001.

Zhang, G., Xie, H., Derosset, L.E., Fedder, G.K., "A lateral capacitive CMOS accelerometer with structural curl compensation", IEEE International MEMS '99, Twelfth IEEE International Conference on Micro Electro Mechanical Systems, 1999, pp. 606-611.

McGill, R.A., Chung, R., Chrisey, D.B., Pique, A., Mlsna, T.E., Stepnowski, J.L., "Performance optimization of surface acoustic wave chemical sensors", IEEE Transactions on Ultrasonics, Ferroelectrics, and Frequency Control, vol. 45, Issue 5, pp. 1370-1380, 1998.

Muralidharan, G., Wig, A.. Pinnaduwage, L., Hedden, A. D., Thundat, T., Lareau, R.T., "Adsorption-desorption characteristics of explosive vapors investigated with microcantilevers", Ultramicroscopy, vol. 97, pp. 433-439, Mar. 2003.

Fedder, G.K., Santhanam, S., Reed, M.L., Eagle, S.C., Guillou, D.F., Lu, M.S.-C., Carley, L.R., "Laminated high-aspect-ratio microstructures in a conventional CMOS process", Sensors and Actuators A: Physical, vol. 57, Issue 2, pp. 103-110, 1996.

McGill, R.A., Nguyen, V.K., Chung, R., "The "NRL-Sawrhino": a nose for toxic gases", Sensors and Actuators B: Chemical, vol. 65, pp. 10-13, 2000.

McGill, R.A, Mlsna, T.E., Chung, R., "The design of functionalized silicone polymers for chemical sensor detection of nitroaromatic compounds", Sensors and Actuators B: Chemical, vol. 65, pp. 5-9, 2000.

Hierlemann, A., Koll, A., Lange, D., Kerness, N., Hagleitner, C., Brand, O., Vogt, R., Baltes, H., "CMOS based chemical microsensors: components of a micronose system", SPIE Conference in Chemical Microsensors and Applications, vol. 3857, pp. 158-169, 1999.

Betts, T.E., Tipple, C.A., Sepaniak, M.J., et al., "Selectivity of chemical sensors based on micro-cantilevers coated with thin polymer films", Analytica Chimica Acta, vol. 422, Issue 1, pp. 89-99, 2000.

Hughes, R.C., Patel, S.V., Manginell, R.P., "A MEMS based Hybrid Preconcentrator/Chemiresistor Chemical Sensor", Sep. 1, 2002.

Micro Analytical Systems Department Technology—µChemLab Face Sheet, Sandia Corporation, Dec. 30, 2002.

DeRosset, L.,"Investigation of a Micro-Joint Angle Sensor Using MEMS Cilia", Project Report in support of Masters of Science, Carnegie Mellon University, 2000.

International Search Report and written opinion in PCT/05/18446, dated Nov. 27, 2006.

* cited by examiner

MICROELECTRO-MECHANICAL CHEMICAL SENSOR

This application claims the benefit of Provisional Application 60/574,388, filed on May 25, 2004, the disclosure of which is incorporated by reference in its entirety.

BACKGROUND OF THE INVENTION

1. Field of the Invention

This application relates generally to microelectro-mechanical devices, and more particularly, to microelectro-mechanical sensors for detecting chemicals in a gaseous environment.

2. Background Information

Microelectronic and microelectromechanical (MEMS) devices have been used in chemical sensors as discussed in H. Baltes, D. Lange, A. Koll, "The electronic nose in Lilliput," *IEEE Spectrum*, September 1998, pp. 35-38, and in H. P. Lang, R. Berger, F. Battiston, J. P. Ramseyer, E. Meyer, C. Andreoli, J. Brugger, P. Vettiger, M. Despont, T. Mezzacasa, L. Scandella, H. J. Guntherodt, C. Gerber, J. K. Gimzewski, "A chemical sensor based on micromechanical cantilever array for the identification of gases and vapors", *Apply. Phys. A* 66, pp. S61-S64, 1998.

A chemical sensor is a device that converts chemical information into an analytically useful signal, and chemical sensors are important for a variety of industrial and environmental applications, including the detection of hazardous chemicals, quality control in the food, perfume, and beverage industries, and medical applications.

Chemical sensors can include a sorbent layer deposited on an active area of a transducer, as described in R. A. McGill, M. H. Abraham, J. W. Grate, "Choosing polymer coatings for chemical sensors," *CHEMTECH* 24, pp. 27-37, 1994. Conventional chemical sensors utilize transducers which are relatively large and have millimeter sized dimensions. See, for example, D. Diamond, *Principles of Chemical and Biological Sensors*, J. Wiley & Sons Inc. New York, 1998. Current state of the art chemical detectors are typically hand held systems.

SUMMARY OF THE INVENTION

An embodiment of the invention is a microelectro-mechanical sensor that includes an electrostatically actuated first cantilever beam attached at one end to a structure, the first beam having a chemically selective material layer disposed thereon and at least a first resistor with a resistance corresponding to a deflection of the first beam, a second cantilevered beam having a resistor disposed thereon, a third cantilevered beam having a resistor disposed thereon, the first, second, and third resistors being elements of a Wheatstone bridge. The output of the Wheatstone bridge corresponds to the amount of a predetermined chemical agent sorbed by the chemically selective material layer.

Another embodiment of the invention is directed to a microelectro-mechanical sensor including a first beam having at least one end attached to a structure, excitation means for causing the beam to deflect, a first resistor disposed on the first beam, the first resistor having a resistance that changes in response to a deflection of the first beam; and at least one cantilevered beam on each of two opposite sides of the first beam, each of the cantilevered beams having an end attached to the structure, each of the cantilevered beams having a resistor disposed thereon, the first resistor on the first beam and the resistors on the cantilevered beams being elements of a Wheatstone bridge.

BRIEF DESCRIPTION OF THE DRAWINGS

A more complete appreciation of the invention will be readily obtained by reference to the following Description of the Example Embodiments and the accompanying drawings.

DETAILED DESCRIPTION OF THE EXAMPLE EMBODIMENTS

Figure 1:
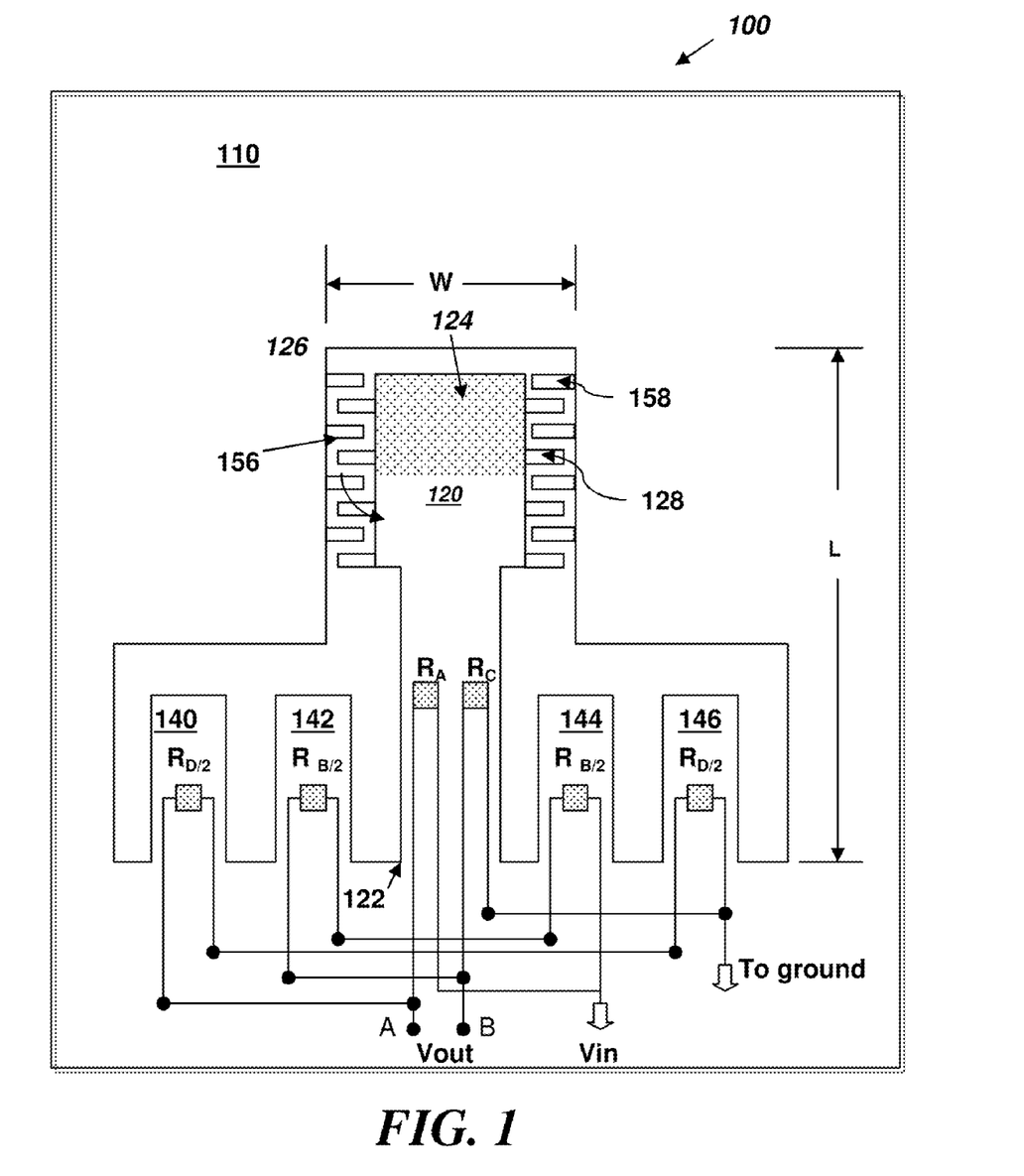
FIG. 1 illustrates a sensor 100 according to an embodiment of the invention.

FIG. 1 illustrates a sensor 100 according to an embodiment of the invention. The sensor 100 has a microelectro-mechanical (MEMs) structure 110 which can be, for example, a complementary metal-oxide-semiconductor (CMOS) device. The sensor 100 includes a cantilever beam 120 which is attached at an end 122 to the MEMS structure 110.

A layer of chemically selective sorbent material 124 is disposed on a surface of the cantilever beam 120. When the sensor is in an environment containing a chemical to which the layer of material is sorptive, the layer of material sobs the chemical, leading to an increase in the mass of the cantilever beam and a modification of the material's viscoelastic properties.

The increase in mass of the cantilever beam 120 will ordinarily result in a decrease in the resonance frequency of the cantilever beam 120, which is indicative of an amount of a target chemical sorbed by the chemically selective material 124. By determining the resonance frequency of the cantilever, the concentration of that chemical in the environment can be determined. In this dynamic mode of operation, the cantilever beam 120 can be actuated at its fundamental resonance frequency. The fundamental resonance frequency in turn depends on the mass loading of the cantilever.

In a static mode of operation, the bending of the cantilever beam 120 upon mass loading and related surface stress is measured. The amount of gas sorbed by the chemically selective material can be determined by the deflection of the cantilever beam 120.

The chemically selective material 124 can be, for example, a polymer layer that is applied to the surface of the microcantilever to enhance its sorptivity to a chemical nerve agent. As one example, the material 124 can be a hexafluoroisopropanol-siloxane polymer that is sensitive to the nerve agent simulant and nerve agent precursor dimethylmethylphosphonate (DMMP).

The sensor also includes excitation means for causing the first cantilevered beam to deflect. In the embodiment illustrated in FIG. 1, the excitation means includes electrostatic actuation components, including, for example, a circuit including a conductor arranged on the cantilever beam 120, and a conductor arranged on an adjacent structure for applying a voltage that acts to deflect the cantilever in a direction out of the plane of the cantilever beam, e.g., upward or downward.

The cantilever 120 preferably has a plurality of protrusions, "combs" or "fingers" 126, 128, arranged on at least one edge 130, 132 of the cantilever. The protrusions 126, 128 are at least partially formed of a conductive material, such as aluminum, so they can be electrostatically actuated by application of a voltage to corresponding protrusions, combs, or fingers 156, 158 on the adjacent chip substrate structure 110. The protrusions 156, 158 are interdigitated with the protrusions 126, 128 on the cantilever 120.

The cantilever beam 120 is an "active" cantilever beam, that is, a cantilever that is suitable to be actively driven. For example, the active cantilever beam 120 is actively driven to be deflected in a direction perpendicular to its plane by electrostatic actuation, and in particular, by applying an voltage across the electrostatic interdigitated fingers or combs on either side of the cantilever beam 120.

The device 100 also preferably includes one or more "auxiliary" or "dummy" cantilever beams 140, 142, 144, and 146 attached at their ends to the structure 110. The auxiliary cantilever beams are cantilevers that are not actively driven. The auxiliary cantilever beams can be located immediately adjacent to the active cantilever beam 120.

Piezoresistors are arranged on the active cantilever beam 120 and on the auxiliary cantilever beams 140, 142, 144, and 146. The piezoresistors are adhered to the beams so that strain in a beam causes a change in resistance of the piezoresistor on that beam.

Figure 2:
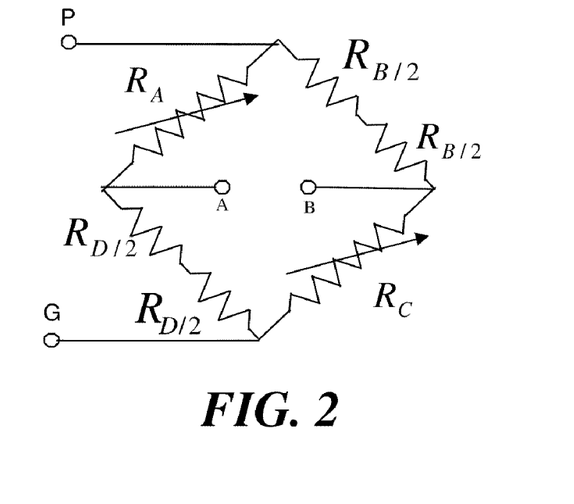
FIG. 2 illustrates a schematic of a Wheatstone bridge according to an exemplary embodiment of the invention.

The piezoresistors are elements of a Wheatstone bridge circuit that outputs a voltage signal indicative of the deflection of the active cantilever beam 120. FIG. 2 illustrates a schematic of a Wheatstone bridge 200 according to an exemplary embodiment of the invention. The piezoresistors on the auxiliary cantilever beams 140, 142, 144, and 146 form the reference resistors of the Wheatstone bridge. The auxiliary cantilever beams are subjected to the same heating and environmental effects as the active cantilever beam, however, the auxiliary beams are not subjected to an electrostatically actuated deflection and since they do not include the chemically sorptive material layer 124, they do not experience any significant change in mass due to adsorption of the target chemical. The output of the Wheatstone bridge is therefore insensitive to temperature effects, making the device very sensitive to deflections of the active cantilever due to adsorption of the target chemical.

The chemical sensor 100 described herein also includes means for determining or monitoring the resonance frequency. In this example, the resonance frequency is monitored with a highly symmetrical on-chip Wheatstone bridge arrangement.

Figure 4:
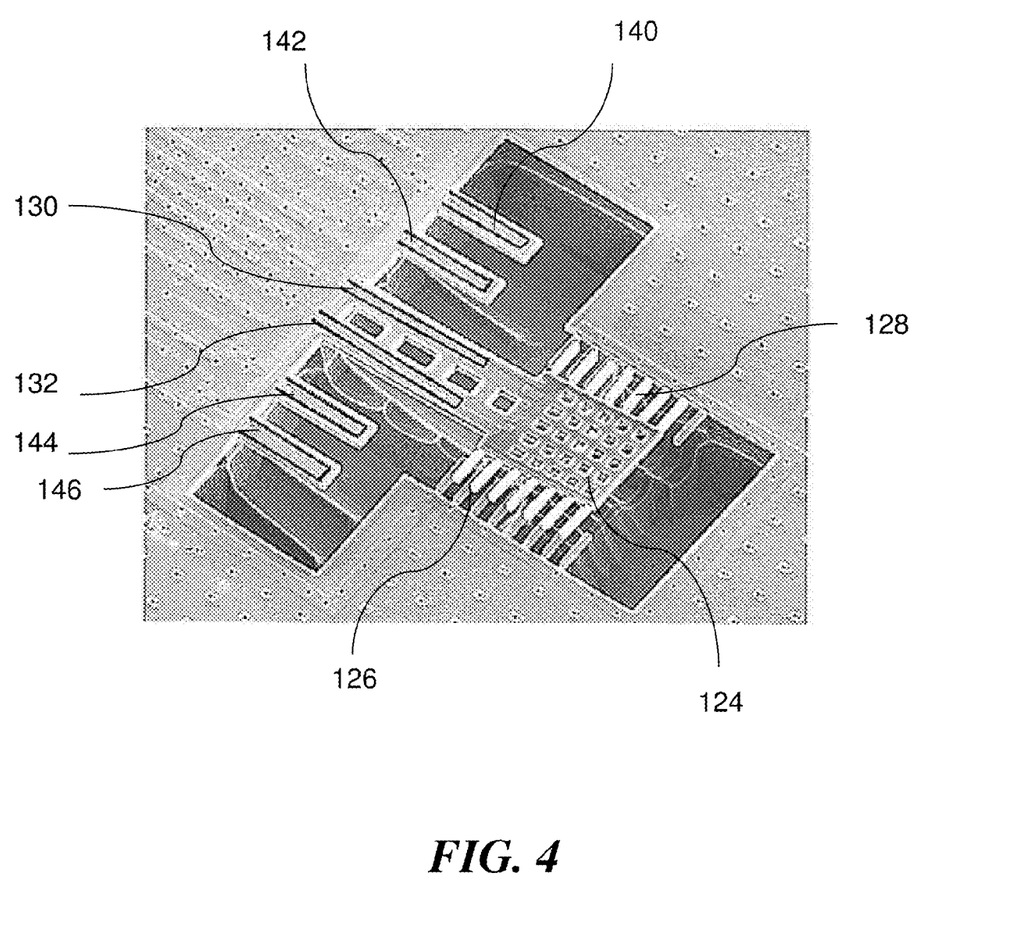
FIG. 4 illustrates a scanning electron micrograph of a portion of the chemical sensor of FIG. 1.

As the active cantilever beam 120 is deflected, the Wheatstone bridge transduces any change in resistance due to the strain experienced by the piezoresistors. Using the Wheatstone bridge configuration, the relative change in the resistance of the piezoresistor is provided as an output voltage signal. In an exemplary embodiment, the Wheatstone bridge has two piezoresistors 130 and 132 ($R_A$ and $R_C$), positioned on the active cantilever beam 120, and two reference resistors $R_B$ and $R_D$ which are situated on neighboring short, auxiliary cantilevers, as shown in FIGS. 1 and 4. Each of the reference resistors $R_B$ and $R_D$ is formed of two resistors in series ($R_{B/2}$ and $R_{B/2}$, $R_{D/2}$ and $R_{D/2}$) positioned in a common-centroid arrangement to allow for improved resistance matching. In particular, each of the resistors $R_{B/2}$, $R_{B/2}$, $R_D/2$, and $R_{D/2}$ that make up the resistances $R_B$ and $R_D$ is arranged on its own auxiliary cantilever on opposite sides of the active cantilever beam 120.

Each of the resistors in the Wheatstone bridge design is micromachined to be positioned on a cantilever, so that on release, each resistor experiences the same changes in stress, and results in a similar degree of curling. This design allows the resistors to maintain their relative matched values before and after release. In addition, this design allows the resistors on the auxiliary cantilevers to experience a similar thermal environment. In particular, the auxiliary cantilevers experience the same heat transfer from the upper and lower surfaces as the active cantilever. This mitigates any effects of temperature, shock, and vibration. Another advantage of this embodiment is that the resistors have equal values of resistance for ease of balancing the Wheatstone bridge.

Figure 3:
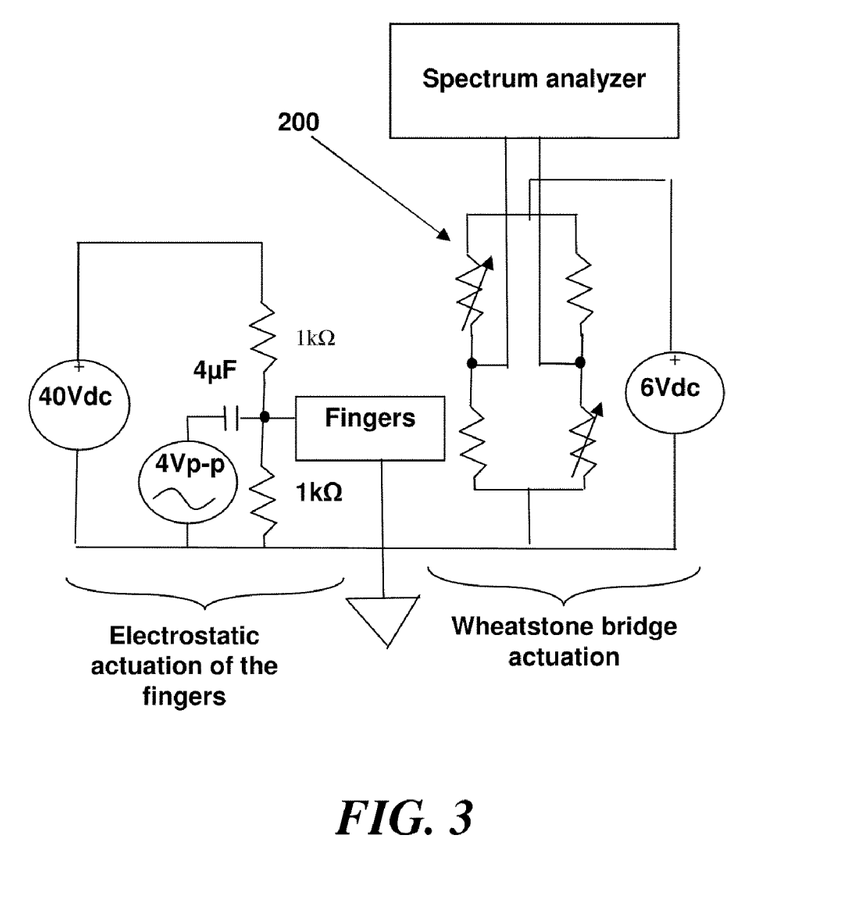
FIG. 3 illustrates suitable circuitry for electrostatically actuating the device and for receiving an output voltage from the Wheatstone bridge according to an embodiment of the invention.

FIG. 3 illustrates suitable circuitry for electrostatically actuating the device and for receiving the output voltage from the Wheatstone bridge 200. As illustrated in FIG. 3, applying an input voltage (e.g., here 6V to ground) across the Wheatstone bridge 200 results in an output voltage $V_{out}$. The dummy cantilevers allow the resistors $R_B$ and $R_D$ fabricated on them to have the same nominal resistance values as the piezoelectric resistors $R_A$ and $R_C$ on the larger, active cantilever beam 120.

The active cantilever beam 120 is deflected from its initial position by applying a voltage between the conductive combs 126, 128 of the active cantilever beam 120 and the conductive combs 156, 158 of the adjacent chip substrate, which are interdigitated with the combs of the active cantilever beam 120.

It is preferred that the combs on the active cantilever beam 120 and the fingers or combs on the chip substrate not be completely planar with each other, e.g., that in the initial position, one set of combs is positioned slightly above or below the plane of the chip 110. This allows the active cantilever's combs 126, 128 to be driven toward or away from the combs 156, 158 of the substrate in a direction out of the plane of the device, initiating an out-of plane deflection of the active cantilever beam 120. In one embodiment, the combs on the substrate adjacent to the active cantilever are flat and are wired to a ground pad. The combs arranged on the active cantilever beam 120 are preferably tilted out of the device plane, and are wired together to a single bond pad, which is connected to an ac drive voltage superimposed on a dc voltage. Combs are preferably arranged on two opposite sides of the active cantilever beam 120, and extend in a direction perpendicular to the length of the cantilever beam 120 and in its plane.

The sensor 100 can be fabricated using a 0.6 µm three metal, double poly CMOS (Complementary Metal Oxide Semiconductor) process, combined with subsequent micromachining steps. A custom polymer layer is applied to the surface of the microcantilever to enhance its sorptivity to an analyte of interest. In a preferred embodiment, the chemically selective polymer is applied to the far end portion of the active cantilever beam and not applied to the portion of the beam closest to the attachment to the chip. This can be achieved by applying micro-droplets of a solution of sorbent onto the substrate area of interest.

The length, width, and thickness of the active cantilever beam 120 can be chosen to optimize various parameters. For example, the cantilever dimensions can be chosen for the best resonance frequency, mass sensitivity, and amount of analyte sorbed. Short, wide, and thick cantilevers are suitable for higher resonance frequencies. The length and width of the cantilever can be made larger to provide larger surface structures that increase the area for sorbent coating and subsequent gas sorption.

A thin layer of sorptive polymer is coated on the cantilever plate surface. This results in a frequency shift of the device to a new signal baseline. In the absence of actual polymer thickness measurements, it is typical to quote the amount of polymer coated as a frequency shift. The uptake of different gases is monitored as an additional shift in the device frequency, which is normally reversible if the gas-polymer chemical interactions are reversible. The cantilever gas sensor acts as a resonating microbalance, with mass increases normally leading to a decrease in the cantilever resonance frequency.

The amount of analyte mass sorbed to the cantilever can be determined from the frequency shift of the cantilever, and the concentration of the gas in the air can be computed according to a calibration curve.

FIG. 4 illustrates a scanning electron micrograph of a portion of the chemical sensor of FIG. 1, marked to show the locations of the piezoresistors, the sorbent coated plate portion of the active cantilever beam 120, and the interdigitated protrusions 126, 128 on the active cantilever beam.

Figure 5:
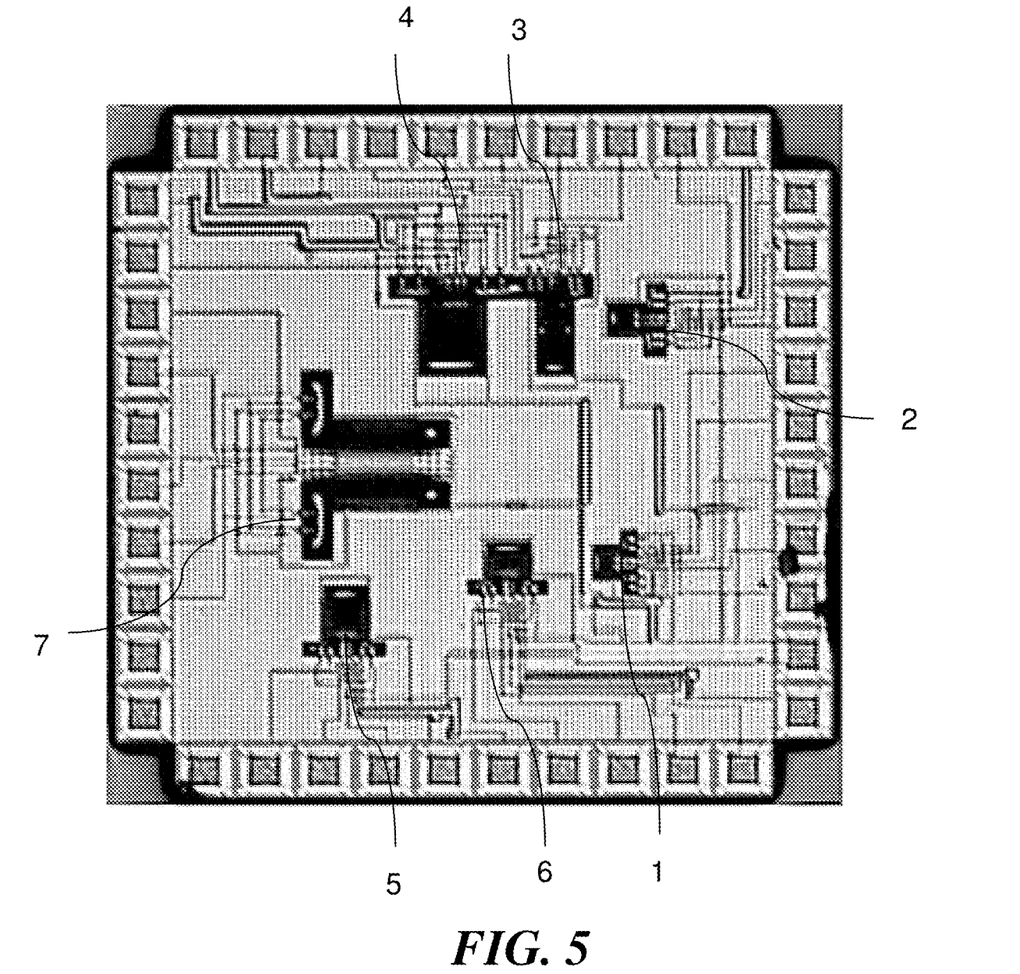
FIG. 5 is a scanning electron micrograph of a CMOS chip having several different microelectromechanical sensors fabricated on a single chip structure in accordance with embodiments of the invention.
Figure 6:
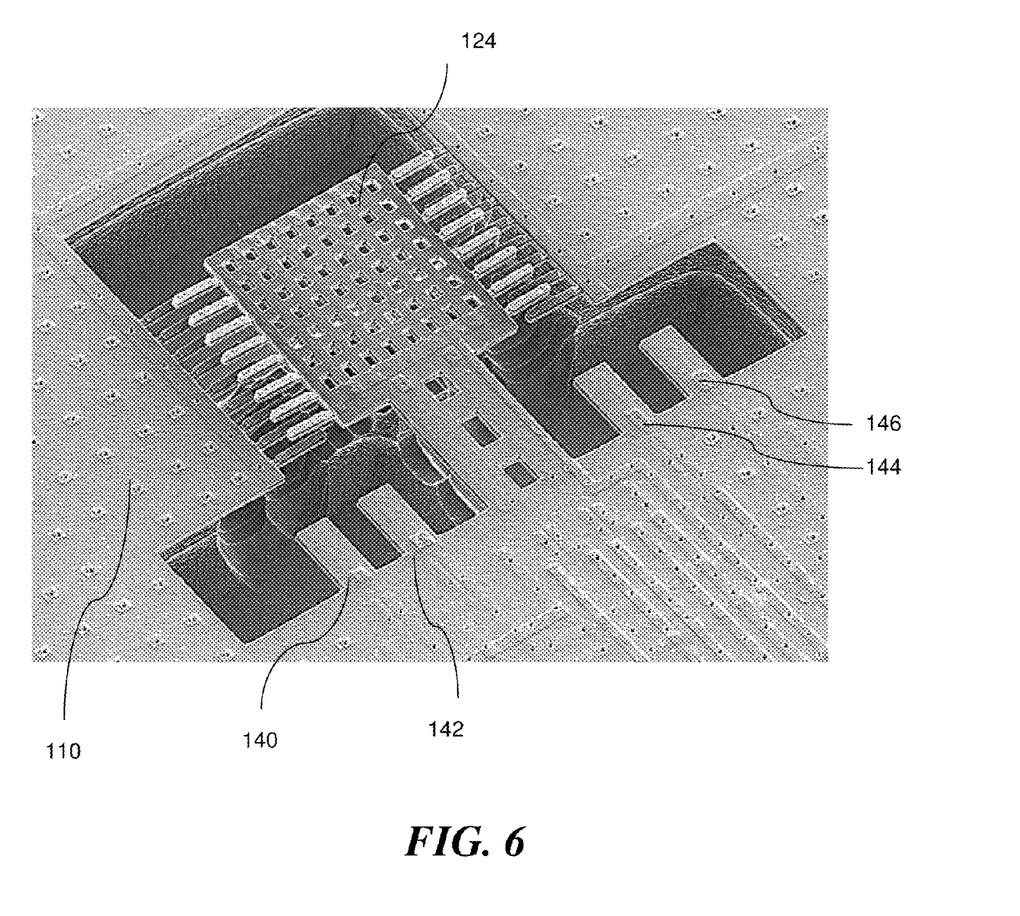
FIG. 6 is a scanning electron micrograph of a portion of a chemical sensor according to an embodiment of the invention.

FIG. 5 illustrates a chemical sensor device having six different cantilever designs 1-6 in a single chip structure with a range dimensions that to illustrate the effect of device shape on resonance frequency and mass sensitivity. In these designs, the length L of the active cantilever beam is varied between 120 µm and 300 µm, and its width W is varied from 60 µm to 150 µm. The uncoated thickness of each beam is 4.2 µm. For example, for the first cantilever, the overall beam length is 125 µm, including a coated plate length of 70 µm. The width of the beam closest to its attachment to the chip is 30 µm and at its widest plate portion is 60 µm. A second of the cantilever sensors has an active cantilever beam that includes two rectangular plate portions, each of which has a sorbent coating on the surface and interdigitated fingers or combs for actuating the microcantilever. The sixth of the cantilever designs is illustrated in FIG. 6. Each of the sensors of FIG. 5 includes a Wheatstone bridge, with reference resistors are arranged on the auxiliary cantilevers in the common-centroid arrangement to allow for improved resistance matching In another embodiment illustrated as bridge 7 in FIG. 5, the active element is a bridge, rather than a cantilever, and is attached to the substrate at each of two ends. The central plate portion is coated with the sorbent material.

For comparison, an alternative embodiment (not shown) includes a piezoresistor Rx on the active cantilever beam, and three piezoresistors $R_1$, $R_2$, and $R_3$ arranged on the adjacent silicon substrate, with no dummy or auxiliary cantilevers. An excitation voltage $V_{in}$ is applied across two opposite ports of the bridge, the output voltage $V_{out}$ changes according to the changes in the resistors under deformation. When Rx is the piezoelectric transducer on the cantilever beam, and $R_1$, $R_2$, and $R_3$ are arranged on the substrate, the reference resistors will have different values than the piezoresistor Rx, due to residual stress from device fabrication and release. The curvature of the armature due to residual stress also influences the nominal value of the piezoresistor. In addition, because Rx is arranged on a cantilever having different thermal transfer characteristics than the substrate, the resistors $R_1$, $R_2$, and $R_3$ will not match the resistance of the piezoresistor Rx at different temperatures.

Other possible embodiments place the resistors $R_1$, $R_2$, and $R_3$ in external circuitry. This arrangement will require a larger surface for the Wheatstone bridge. In addition, it is difficult to predict the nominal value of the released resistance for this arrangement, in order to connect identical external resistances. Further, when just one of the resistors in the Wheatstone bridge is arranged on a cantilever, the output voltage Vout is dependent on the value of Rx, which is directly proportional to the strain on the cantilevered beam. For a balanced bridge circuit, $R_1 = R_2 = R_3 = R_0$, and $Rx = R_0(1+X)$, where X is the percent change in resistance due to strain ($\epsilon$). Further, $V_{out} = V_{in}(X/4)$ and $V_{out} = V_{in}\epsilon(GF/4)$. If the gauge factor GF and the input voltage $V_{in}$ are known, the strain on the beam or membrane can be directly related to the output voltage of the Wheatstone bridge. For improved accuracy of the measurements, the Wheatstone bridge has to be perfectly balanced, e.g., the resistors on the substrate and the resistors on the cantilever should have matching resistance values. However, the reference resistors will have different values than the piezoresistor Rx, due to residual stress from device fabrication and release. The curvature of the armature due to residual stress also influences the nominal value of the piezoresistor. In addition, this arrangement is also sensitive to temperature changes, shock, and vibration.

In contrast, the preferred embodiments discussed above, which place the reference resistors on auxiliary cantilevers, facilitate balancing of resistance values, and are insensitive to temperature, shock, and vibration.

It will also be apparent that the Wheatstone bridge arrangement of FIG. 1, discussed above, will provide a balanced Wheatstone bridge arrangement that is temperature, shock, and vibration insensitive for other MEMS cantilever applications. For example, the Wheatstone bridge arrangement is suitable for MEMS devices such as accelerometers, pressure sensors, gyroscopes, and microphones.

Without being bound by the following, the following description is provided for a fuller appreciation of the features of the embodiments of the inventions.

The natural frequency of a simple undamped rectangular cantilever is defined in W. T. Thomson, *Theory of Vibration with Applications*, Prentice Hall, 1993, 4$^{th}$ Edition as:

$$f = \frac{3.51}{2\pi}\sqrt{\frac{EI}{mL^4}}$$

where E, I, m, and L are the Young's modulus, area moment of inertia about the neutral axis, mass per unit length, and length of the cantilever, respectively.

The natural frequency for the free undamped vibration of a composite cantilever can be expressed by replacing the bending stiffness (EI) and mass per unit length (m) terms from equation (1) with composite bending stiffness and composite mass per unit length. The resonance frequency for a composite cantilever is given by:

$$f = \frac{3.51}{2\pi}\sqrt{\frac{\sum_{i=1}^{N} E_i I_i}{L^4 \sum_{i=1}^{N} m_i}}$$

where N is the number of layers of the composite cantilever, $E_i$, $I_i$, and $m_i$ are the effective Young's modulus, the moment of inertia and the mass per unit length, of each layer respectively.

For a microcantilever, and a uniformly deposited mass, the gravimetric change, $\Delta m$, can be estimated with:

$$\Delta m \approx \frac{k}{\pi^2}\left(\frac{1}{f_1^2} - \frac{1}{f_2^2}\right)$$

where $f_1$ and $f_2$ are the resonant frequencies of the cantilever before and after absorption, and k is the spring constant.

The spring constant k for a composite cantilever with a uniform cross-section can be represented by:

$$k = \frac{3\sum_i E_i I_i}{L^3}$$

with $E_i$ and $I_i$ denoting the effective Young's modulus and the moment of inertia of the individual layers of the cantilever, respectively.

The amount of gas sorbed to the sorbent coating depends on the specific gas-sorbent material interactions, the amount of sorbent material, and the analyte concentration in the sampled environment. At a molecular level, the analyte molecules diffuse in and out of the sorbent material film, and the concentration in the sorbent material rises until a dynamic equilibrium is reached. For analyte molecules that are strongly bound to the sorbent material, desorption can be facilitated by the operation of a heater included in the sensor system.

An embodiment of the invention is a sensor that includes an array of cantilever sensors with each cantilever coated with a different sorbent material, in which the pattern of responses that results from analyte exposure can be used to identify the gas.

The microcantilever is preferably formed using CMOS technology, with post-process micromachining that allows for integration of sensors and circuitry on the same chip. The microcantilever can include multilayers of silicon oxide, silicon nitride, polysilicon, and aluminum thin films, for example.

Suitable two and three metal layer combinations for forming the cantilevers are described in Voiculescu, I.; Zaghloul, M.; McGill, R. A., "Design, Fabrication, and Modeling of Microbeam Structures for Gas Sensors in CMOS Technology"; Circuits and Systems, 2003, ISCAS '03, Proceedings of the 2003 International Symposium Volume 3, 25-28 May 2003 Page(s): III-922-III-925, and in D. F. Guillou, S. Santhanam, L. R. Carley, "Laminated, sacrificial-poly MEMS technology in standard CMOS," Sensors and Actuators, Vol. 85 (2000), p. 346-355. The manufacturing process can include metallization as an etch-resistant mask to define the microstructures. The microstructural layers of the cantilever sensor device can be designed with any of the three meal layers as the etch mask, with their thickness being a function of the number of metal masking layers. In most surface micro-machined technologies, the design control is limited to two planar dimensions of a mechanical structure. One advantage of CMOS technology is that the design can be based on the availability of up to three metal layers, which offers the design flexibility in a third dimension. Using different combinations of the three metal layers, different cantilever thicknesses can be fabricated. The chips in the FIG. 4 and FIG. 6 embodiments had an uncoated thickness of 4.2 µm.

The sensors described herein can be manufactured by any suitable CMOS technology. One example of a suitable process as follows.

The post-processed structures fabricated using Carnegie Melon University (CMU) CMOS-MEMS technology with the Austria Microsystems (AMS) CMOS process can exhibit curling after release. The CMOS metal and dielectric layers, which form the laminated structures, have different coefficients of thermal expansion, which can result in the curling of the released structures.

An example of a chip was designed with a CMU CMOS-MEMS chip design technique using MEMSCAP-Xplorer software installed under Cadence, using a die size of 2.5 mm by 2.5 mm. The foundry used in this work is based on the AMS process (0.6 µm, 3-metal, 2-poly CMOS). The standard CMOS-MEMS process is followed by two maskless dry etch steps to release the microstructures that are protected by the top-most metal layer. An anisotropic reactive ion etch (RIE) process with $CHF_3$ and $O_2$ is first used to remove the silicon oxide not covered by any of the aluminum metal layers. This step is followed by an isotropic RIE process using $SF_6$ and $O_2$ to remove the underlying silicon, and release the microstructure.

In the cantilever sensor devices described herein, the cantilever is electrostatically actuated perpendicular to the curling of the cantilever structures, so the device curling is not a negative design issue for this application. In the chip layout, suitable gaps are included to permit the RIE post processing step.

A suitable sorbent material for sorbing nerve gas agents or the nerve gas simulant dimethylmethylphosphonate (DMMP) is HCSA2. HCSA2, other polymers and sorbent materials are described in E. J. Houser, D. L. Simonson, J. L. Stepnowski, R. A. McGill, "Linear and Hyperbranched Hydrogen Bond Acidic Poly(silylene methylene)s for Chemical Sensor Applications" PMSE Preprints 2003, 88, 548, in R. A. McGill, M. H. Abraham, J. W. Grate, "Choosing polymer coatings for chemical sensors," *CHEMTECH* 24, pp. 27-37, 1994, and in U.S. Pat. No. 6,660,230 to R. A. McGill, and E. J. Houser, entitled "Linear chemoselective carbosilane polymers and methods for use in analytical and purification applications", the disclosure of which is incorporated by reference in its entirety.

Each of the active cantilever beams is coated on its wider plate portion with a dilute solution of polymer HCSA2 in Chloroform (0.03% w/w) with a piezo inkjet dispensing head. The dispensed drop is directed at the desired location on the cantilever plate by viewing the cantilever through a microscope during the coating process. It is preferred to avoid depositing excessive amounts of polymer on the interdigitated fingers which would prevent oscillation.

Figure 7:
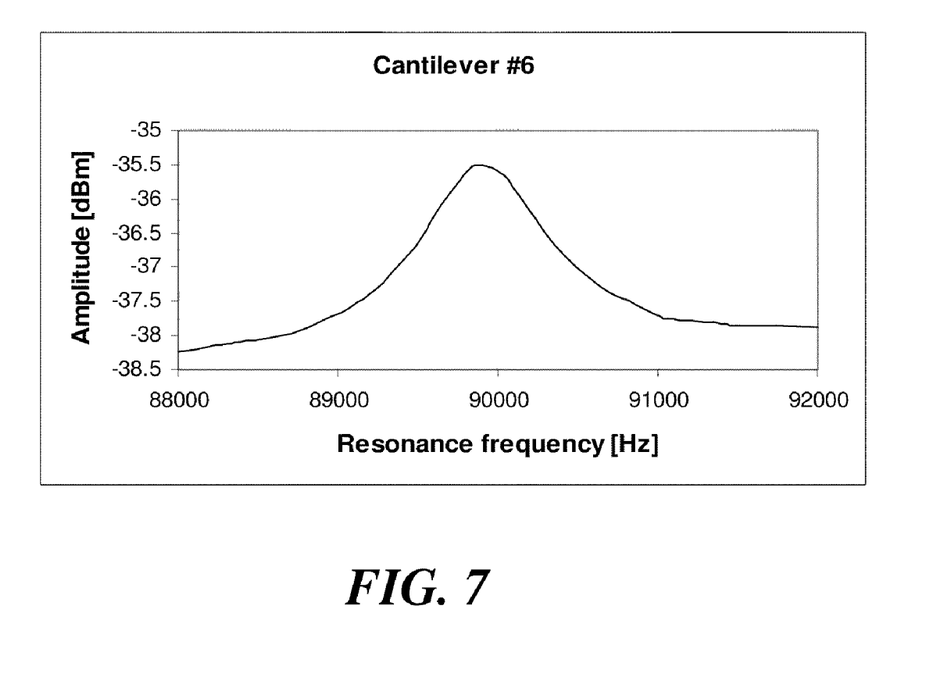
FIG. 7 illustrates the resonance frequency of a cantilever gas sensor in accordance with one embodiment of the invention.
Figure 8:
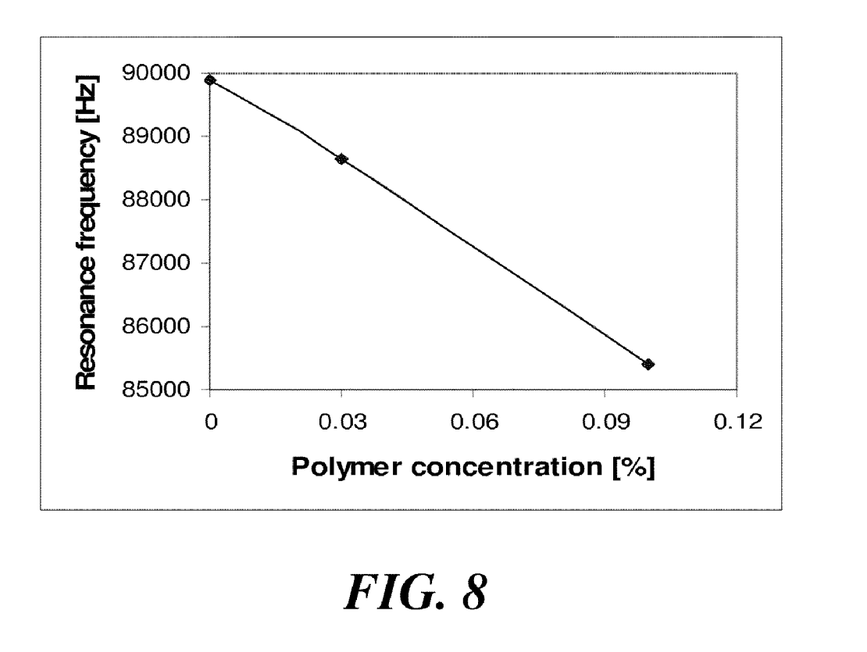
FIG. 8 is a graph illustrating the change of sorbent coated cantilever resonance frequency as a function of the concentration of deposited polymer for the embodiment of FIG. 6, for a deposited solution of the same volume.

Cantilever 6 from the chip was coated with a single drop of polymer solution. The resonance frequency of the cantilever before coating was 89.9 KHz, as illustrated in FIG. 7. The resonance frequency can be adjusted as desired, by depositing a higher or lower polymer concentration, as illustrated in FIG. 8.

To electrically characterize the cantilever gas sensors, the applied voltage at the input of the Wheatstone bridge for each of the six sensors of Table 1 was set at 6 V. The offset voltage of the Wheatstone bridge, when the cantilever was not actuated, was between 2-20 mV depending on the cantilever design. The resistance measurements were performed with a Summit 11651-6 Thermal Probe Station, with a Keithley 2400 source meter, using Cascade Microtech DCP 150R Precision DC probes.

The resonance frequencies from the ANSYS simulations and the measured lowest order resonance frequencies of the six cantilevers fabricated on the chip are provided in Table 1.

Each of the sensors can be excited electrostatically by applying a dc voltage, which results in attractive Coulombic forces between the interdigitated fingers. The cantilevers are set into oscillatory motion in a plane perpendicular to the cantilever.

With a dc voltage of 23 V applied to the fingers of cantilever device 6, the device deflects towards the support by 0.53 µm, which is large enough for the electrostatic actuation of the cantilever.

The dc polarization voltage is applied between the electrodes fingers to create a surface charge and an ac voltage is superimposed to drive the device with a harmonic force. The dc voltage applied from an Agilent E3631A power supply to deflect the cantilevers was 20 V, and an ac voltage of 4 V peak to peak from a Hewlett Packard HP 3588A spectrum analyzer drove the oscillation of the cantilever. At the resonance frequency, the Wheatstone bridge output signal was measured between 80 mV and 120 mV, depending on the dimensions of each cantilever, with the Wheatstone bridge biased at 6 V. The resonance frequency simulations with ANSYS were useful to narrow the frequency range monitored by the spectrum analyzer. The resonance frequencies stimulated with ANSYS and measured with the circuitry are in good agreement and are shown in Table 1. The differences maybe in part explained by an incomplete simulation that does not include the fingers and etch release holes on the surface of the active cantilever beam.

TABLE 1

| Cantilever # | Simulation results [KHz] | Measured electrically [KHz] |
|---|---|---|
| 1 | 113.773 | 111.550 |
| 2 | 92.380 | 90.300 |
| 3 | 26.600 | 25.400 |
| 4 | 29.900 | 27.350 |
| 5 | 54.100 | 53.680 |
| 6 | 91.360 | 89.900 |

The cantilever's resonance frequency shift response resulting from analyte sorption increases with increasing thickness of the sorbent layer. At equilibrium, the thicker the sorbent layer will sorb more analyte molecules, with a larger mass change to detect.

The concentrations of HCSA2 polymer used on the sensors of FIG. 5 are 0.03% w/w, and 0.1% w/w in chloroform. The inkjet nozzle has an internal diameter of 30 µm, however the dispensed drop diameter is larger and estimated to be 40 µm. The cantilever plate coated with the sorbent material had the dimensions 50 µm×60 µm. To avoid any high temperature process after sorbent material coating, the chip is wire bonded onto a Kyocera DIP 40 ceramic package in advance of the coating deposition.

The cantilever beam frequency shift as a function of the amount of sorbent material or droplet concentration is shown in FIG. 8, which shows a linear relationship over the range tested. The deposition of the sorbent material leads to a decrease in resonance frequency, with a simultaneous decrease in the vibrational amplitude and a degradation in the device Q.

The vapor used for cantilever testing can be generated by bubbling dry $N_2$ (6-0.3 ml/min) through a thermostatted glass container maintained at 15° C., and diluted from near saturation with a relatively large volume of purified air (100-2500 ml/min). Pneumatic tubing used for all gas wetted parts can be PFA. The chip mounted in the Kyocera package is sealed by positioning a lid manufactured by Chelsea Technology and known by the tradename COMBO LID™ over the device package and sealing the peripheral edges by applying tape. The lid can be modified by drilling two holes. A single PFA inlet tube (i.d.=0.125") is attached to one of the holes situated directly above the chip, so that airflow was perpendicular to the cantilever. The second hole allows air and vapor to exhaust away from the device. The majority of the vapor test measurements are carried out with a constant flow rate (6 ml/min) through the DMMP, and by carrying the diluent air from 100 to 2500 ml/min. Above 2500 ml/min, the noise of the cantilever becomes excessive. The airflow is delivered at a temperature of 20° C., with a relative humidity of 0%. The sealed chip manifold is not actively temperature controlled. The vapor on and off time periods can be set at 5 minutes or the time required to reach an equilibrated response.

During vapor tests, the cantilever (cantilever 6) is operated in a resonant frequency mode and the sensor response is monitored as a shift in the resonance frequency. The frequency sweep, with a resolution of 5 Hz, over the complete 3 KHz range can be set at 5 s. The graphical frequency data, and the resonant frequency can be displayed on the spectrum analyzer. Initially, tests are carried out by exposing a bare cantilever to DMMP vapor at elevated concentrations, showing no measurable frequency shift. The same chip can be then coated with a single drop of sorbent material solution at two different concentrations (0.03% w/w in chloroform). This device is then exposed to DMMP vapor at concentrations which were ramped from 43 mg/m$^3$ to 0.1 mg/m$^3$ in a repeated fashion.

Figure 9:
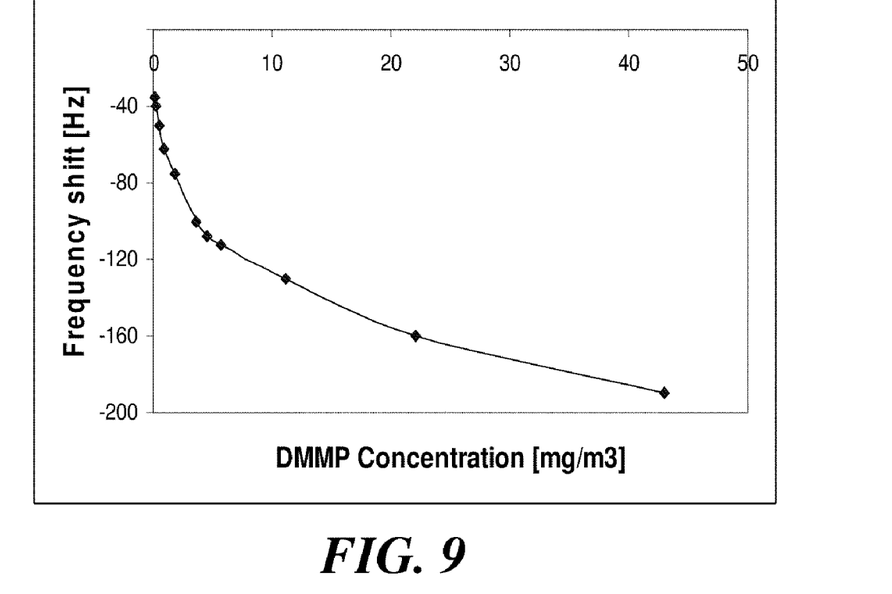
FIG. 9 is a graph illustrating the sorbent coated cantilever response as a function of the concentration of target chemical dimethylmethyl phosphonate (DMMP) for the embodiment of FIG. 6.
Figure 10:
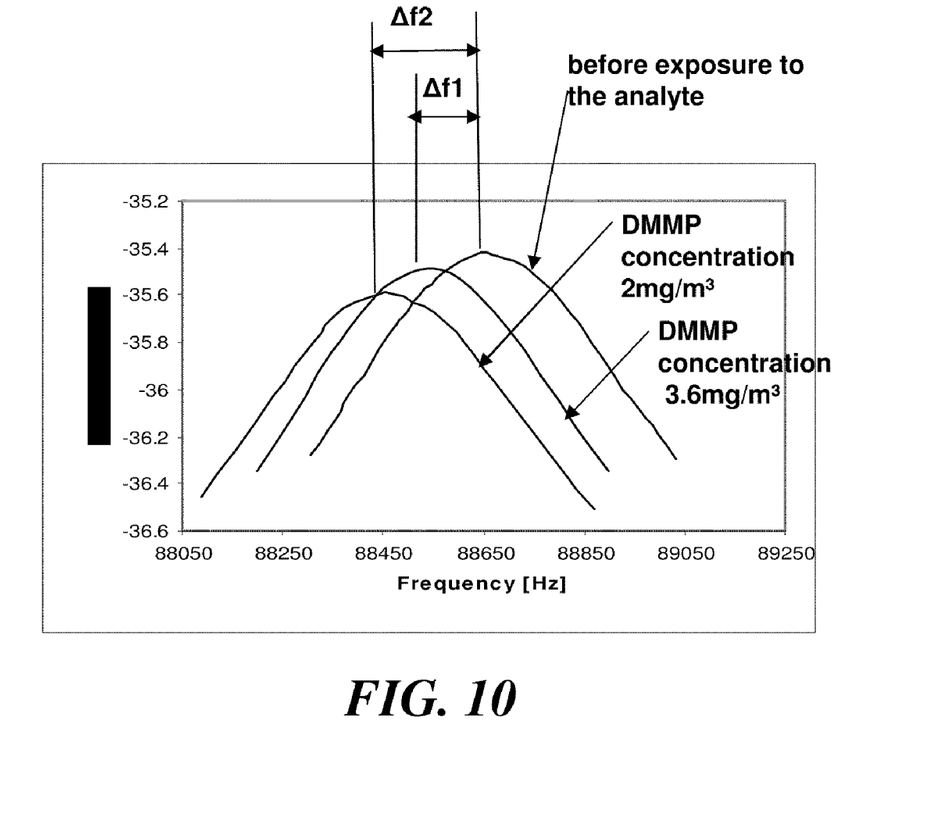
FIG. 10 illustrates the sorbent coated cantilever amplitude and frequency response to different concentrations of target chemicals for the embodiment of FIG. 6.

The sorbent material thickness can be estimated from the known solution concentration, the approximate drop volume, and the surface area covered. The computed mean thickness is 335 nm. At this thickness, the sensor time constant to 90% of signal is approximately 10 s. Example frequency sweeps taken from the spectrum analyzer are shown in FIG. 9. The cantilever sensor response as a function of DMMP concentration is shown in FIG. 9 and FIG. 10. The lowest DMMP concentration tested is 0.1 mg/m$^3$ or 20 ppb. At this concentration, the signal frequency shift was 40 Hz, with an estimated signal noise level of 10 Hz. The time constant for the signal response was of the order of ten seconds to reach ninety percent of equilibrated signal.

The chemical sensors described herein offers an inexpensive option for mass production of a miniature chemical detector, which contains on chip electronics integrated to the cantilever. The devices described herein, when provided with a thin layer of HCSA2 polymer on a surface of the active cantilever, provide highly sensitive chemical sensors for the nerve agent class of chemical warfare materials.

The apparatus can also be combined with integrated electronic circuitry. The sensors described herein allow on chip electronics to be provided at low costs and with high production yields. In addition, other micromachined analytical system components can be combined together to fabricate a micro gas analyzer. These components may include a micromachined preconcentrator, gas chromatograph, and air pumping system.

The detector is useful for monitoring the presence of hazardous chemicals in the air, for both civilian ad military applications, and in particular, is useful as a highly sensitive, accurate, and rapid detector for chemical agents and toxic industrial chemicals. A number of detectors can be distributed over a wide geographical area, or one or more detectors can be combined in an unobtrusive pager-like device and worn by an individual.

Obviously, many modifications and variations of the present invention are possible in light of the above teachings. It is therefore to be understood that the claimed invention may be practiced otherwise than as specifically described.

What is claimed is:

1. A microelectronics based chemical sensor comprising:
   a first active beam having at least one end attached to a structure and a chemically selective material layer disposed on the first active beam;
   excitation means for causing the first active beam to deflect;
   a first resistor disposed on the first active beam, the first resistor having a resistance that changes responsive to a deflection of the first active beam; and
   two reference cantilevered beams disposed on each side of the first active beam, each of the reference cantilevered beams having a resistor disposed thereon, wherein the first active beam and the reference cantilevered beams are arranged within a same aperture of the structure and extend in a same direction within the aperture,
   the first resistor on the first active beam and the resistors on the reference cantilevered beams being elements of a Wheatstone bridge,
   wherein an output of the Wheatstone bridge corresponds to an amount of a chemical sorbed by the material layer.

2. A sensor according to claim 1, wherein the first active beam is a cantilevered beam.

3. The sensor according to claim 2, wherein the first active cantilevered beam has a length of between about 50 micrometers and about 300 micrometers and a width of between about 50 micrometers and about 150 micrometers.

4. The sensor according to claim 1, wherein the first resistor and the resistors on the reference cantilevered beams are piezoresistors.

5. A sensor according to claim 1, further comprising:
   a second resistor on the first active beam, the second resistor having a resistance corresponding to a deflection of the first beam, the second resistor being an element of a different arm of the Wheatstone bridge than the first resistor on the first active beam and the resistors on the reference cantilevered beams.

6. The sensor according to claim 1, wherein a first reference arm of the Wheatstone bridge includes the resistors disposed on two of the reference cantilevered beams on opposite sides of the first active beam, and a second reference arm of the Wheatstone bridge includes the resistors disposed on a different two of the auxiliary cantilevered beams on opposite sides of the first active beam.

7. The sensor according to claim 1, wherein the resistors on the first active beam and on the reference cantilevered beams comprise polysilicon.

8. The sensor according to claim 1, wherein the Wheatstone bridge measures a resonance frequency of the first active beam.

9. The sensor according to claim 1, wherein the chemically selective material comprises a hexafluoroisopropanol-siloxane polymer.

10. The sensor according to claim 1, wherein the excitation means includes electrical conductors disposed on the first active beam that carry an electrical charge for electrostatic actuation of the first active beam.

11. The sensor according to claim 1, wherein the excitation means includes a plurality of electrically conductive protrusions on the first active beam interdigitated with protrusions on the structure, the protrusions on the first active beam and the protrusions on the structure carrying electrical charges for electrostatic actuation of the first active beam.

12. The sensor according to claim 1, wherein at least two edges of the first active beam have a plurality of electrically conductive protrusions interdigitated with electrically conductive protrusions on the structure extending from the structure toward the first active beam.

13. The sensor according to claim 1, wherein the resistors comprise polysilicon.

14. The sensor according to claim 1, wherein the structure is a CMOS device.

15. The sensor according to claim 1, wherein the chemical is nerve agent simulant dimethylmethylphosphonate or a nerve agent.

16. The sensor according to claim 1, wherein a first of the arms of the Wheatstone bridge includes two of the resistors disposed on two of the reference cantilever beams on opposite sides of the first active beam and closest to the first active beam, and a second of the arms of the Wheatstone bridge includes a different two of the resistors disposed on a different two of the auxiliary cantilevered beams on opposite sides of the first active beam and farthest from the first active beam.

17. The sensor according to claim 1, wherein the reference cantilever beams are substantially free of the chemically selective material layer.

18. A microelectronics based chemical sensor comprising:
   an electrostatically actuated first cantilever beam attached at one end to a structure, the first active beam having a chemically selective material layer disposed thereon;
   at least a first resistor disposed on the first cantilever beam, the first resistor having a resistance corresponding to a deflection of the first cantilever beam,
   a second cantilever beam having a second resistor disposed thereon, the second cantilever beam attached at an end to the structure on one side of the first cantilever beam;
   a third cantilever beam having a third resistor disposed thereon, the third cantilever beam attached at an end to the structure between the first cantilever beam and the second cantilever beam;
   a fourth cantilever beam having a fourth resistor disposed thereon, the fourth cantilever beam attached at an end to the structure at an opposite side of the first cantilever beam; and
   a fifth cantilever beam having a fifth resistor disposed thereon, the fifth cantilever beam attached at an end to the structure between the first cantilever beam and the fourth cantilever beam;
   the first, second, third, fourth and fifth resistors being elements of a Wheatstone bridge,
   a measuring arm of the Wheatstone bridge comprising the first resistor,
   a reference arm of the Wheatstone bridge comprising the second and fourth resistors in series, and another reference arm of the Wheatstone bridge comprising the third and fifth resistors in series, the output of the Wheatstone bridge corresponding to the amount of an analyte sorbed by the chemically selective material layer.

19. The sensor according to claim 18, the Wheatstone bridge having an output that corresponds to the resonance frequency of the first cantilever beam.

20. The sensor according to claim 18, wherein the structure is a CMOS chip.

21. The sensor according to claim 18, further comprising:
conductive protrusions on at least one edge of the first cantilever beam, said conductive protrusions being interdigitated with conductive protrusions on the structure, the conductive protrusions carrying electrical charges for electrostatic actuation of the first cantilever beam.

22. The sensor according to claim 18, wherein the chemical is nerve agent simulant dimethylmethylphosphonate or a nerve agent.

23. The sensor according to claim 18, wherein the second, third, fourth, and fifth cantilever beams are substantially free of the chemically selective material layer.

24. The sensor according to claim 18, further comprising:
a sixth resistor arranged on the electrostatically actuated first cantilever beam,
the Wheatstone bridge including another measuring arm comprising the sixth resistor.

* * * * *